(12) United States Patent
Nemoto et al.

(10) Patent No.: US 7,265,229 B2
(45) Date of Patent: Sep. 4, 2007

(54) METHOD FOR SYNTHESIZING MACROSPHELIDES

(75) Inventors: Hideo Nemoto, Toyama (JP); Yu-ji Matsuya, Imizu-gun (JP)

(73) Assignee: Lead Chemical Co., Ltd., Toyama (JP)

( * ) Notice: Subject to any disclaimer, the term of this patent is extended or adjusted under 35 U.S.C. 154(b) by 304 days.

(21) Appl. No.: 10/535,136

(22) PCT Filed: Nov. 26, 2002

(86) PCT No.: PCT/JP02/12304

§ 371 (c)(1),
(2), (4) Date: Jun. 22, 2005

(87) PCT Pub. No.: WO2004/048360

PCT Pub. Date: Jun. 10, 2004

(65) Prior Publication Data

US 2006/0030720 A1 Feb. 9, 2006

(51) Int. Cl.
*C07D 323/00* (2006.01)

(52) U.S. Cl. ...................................... 549/267

(58) Field of Classification Search .................. 549/267
See application file for complete search history.

(56) References Cited

OTHER PUBLICATIONS

Nakamura et al., Chem. Pharm. Bull. (2002), vol. 50(2), p. 303-36.*
Ono et al., Tetrahed: Asym. (2000), vol. 11, p . 2753-64.*
Nakamura et al., Hetrocy. (2002), vol. 57(2), p. 327-36.*
Nakamura et al., Dai 42 Kai Symp: Chem. of Natural Products (Oct. 1, 2000), Symp. Papers, p. 637-42.*

Cox et al., J. Chem. Perkins Trans. 1 (1991), vol. 8, p. 1901-05.*
Trost et al., Tetrahed. Letts. (1986), vol. 27(47), p. 5691-94.*
* Cited in the ISR of PCT/JP02/12304.*

* cited by examiner

*Primary Examiner*—Taofiq Solola
(74) *Attorney, Agent, or Firm*—Oliff & Berridge PLC

(57) ABSTRACT

The present invention is a method for synthesizing macrosphelides represented by the following formula, and relates to the following method. The hydroxyl group of methyl 3-hydroxybutyrate is protected and reduced to alcohol. The alcohol is then oxidized to give 3-(tert-butyldimethylsilyloxy) butylaldehyde, and this aldehyde is then reacted with tert-butyl diethylphosphonoacetate to give an olefin, and then deprotected. Next, dehydrative condensation with diethylphosponoacetic acid are performed to give tert-butyl 5-[2-(diethylphosphonoyl) acetoxy] hex-2-enoate, and this compound is reacted with 3-(tert-butyldimethylsilyloxy) butylaldehyde to form a diester. Following this, deprotection is performed to give an alcohol, and dehydrative condensation of the alcohol with 3-(tert-butyldimethylsilyloxy) butyric acid gives a triester. A hydroxycarboxylic acid is yielded by deprotection, and then the hydroxycarboxylic acid is converted into a macrolactone

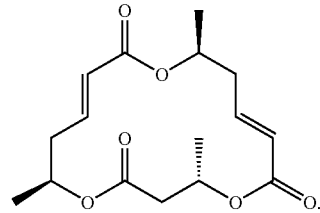

3 Claims, No Drawings

METHOD FOR SYNTHESIZING MACROSPHELIDES

FIELD OF THE INVENTION

The invention relates to a novel method for synthesizing macrosphelides, which display cell adhesion inhibition activity and are gaining attention as a lead compound for development of new anti-cancer drugs.

BACKGROUND OF THE INVENTION

Macrosphelides are macrolide compounds that have a 16-membered ring structure. For example, isolation and structure determination of known macrosphelides A to L, which are expressed by the following formulas, has been achieved using Microsphaeropsis sp. F0-5050 and Periconia byssoides OPUS-N133.

It has been shown by tests on cell adhesion inhibition that macrosphelides can inhibit adhesion of human leukemia cells and human vascular endothelial cells depending on concentration. Further, tests using monoclonal antibody have suggested that this action centers on a particle called Sialyl Lewis, which is a particle that influences reduction of adhesion of leucocyte cells or cancer cells to vascular endothelial cells. Moreover, it has also become apparent that macrosphelides do not cause any significant growth inhibition or have toxicity for various mammals, and thus there are growing expectations for their use as a lead compound for specific cancer spread inhibiting drugs that can be practically applied.

As the noteworthy biological activity of macrosphelides has become clear as described above, recently, research about total synthesis of macrosphelides has started to be reported. At present, as a result of research by two research groups, asymmetric total synthesis of macrosphelides A, B, C and F has been achieved using the convergent synthesis strategies shown below.

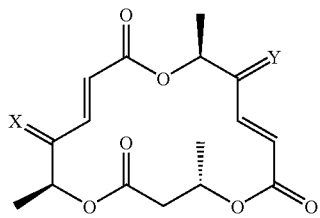
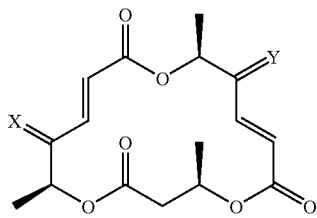

Macrosphelide A: X = α-OH, β-H
                 Y = α-OH, β-H
Macrosphelide B: X = O, Y = α-OH, β-H
Macrosphelide C: X = α-OH, β-H
                 Y = α-OH, β-H Macrosphelide E: X = α-OH, β-H
                 Y = α-OH, β-H
Macrosphetide F: X = α-OH, β-H
                 Y = α-H, β-H
Macrosphelide G: X = α-H, β-H
                 Y = α-OH, β-H

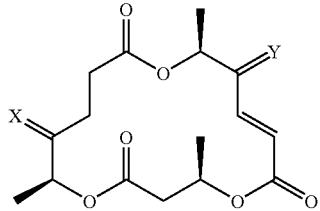
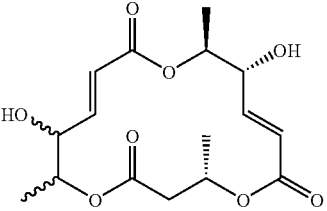

Macrosphelide I: X = α-OH, β-H
                 Y = α-OH, β-H
Macrosphelide L: X = O, Y = α-OH, β-H Macrosphelide D

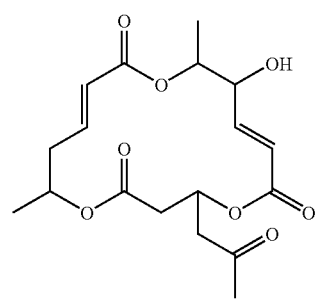
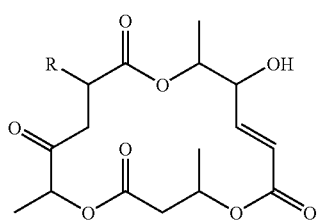

Macrosphelide H

Macrosphelide J: R = OCH$_3$
Macrosphelide K: R = OC$_2$H$_5$

Method 1:
Asymmetric dihydroxylation
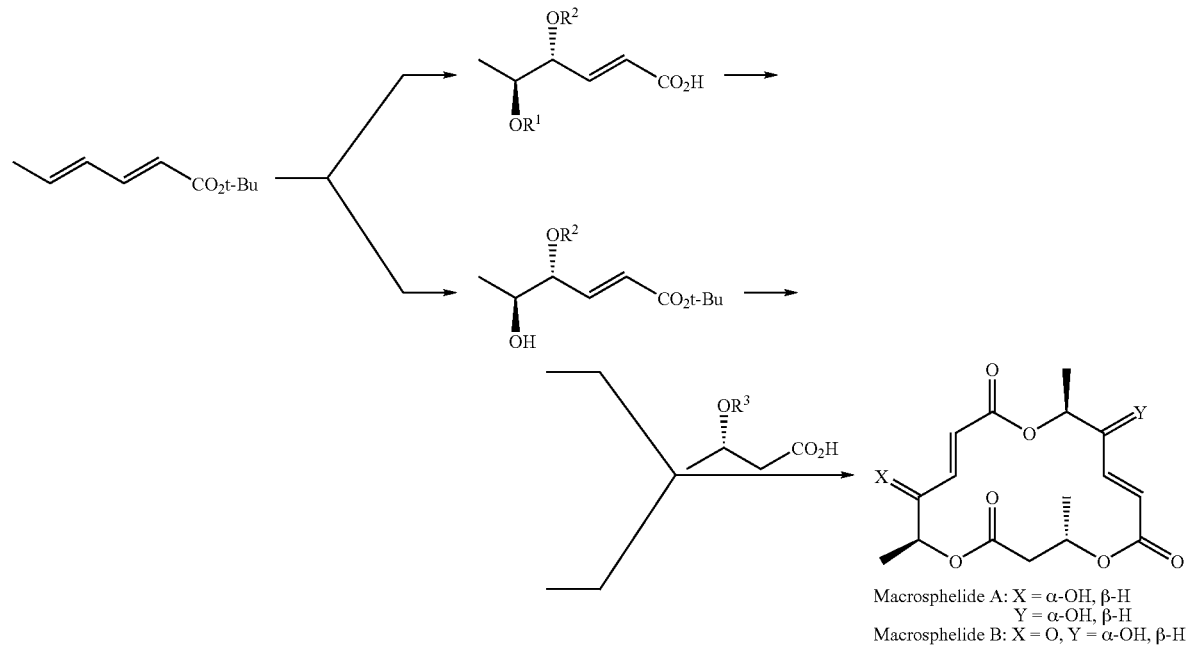
Method 2:
Kinetic analysis
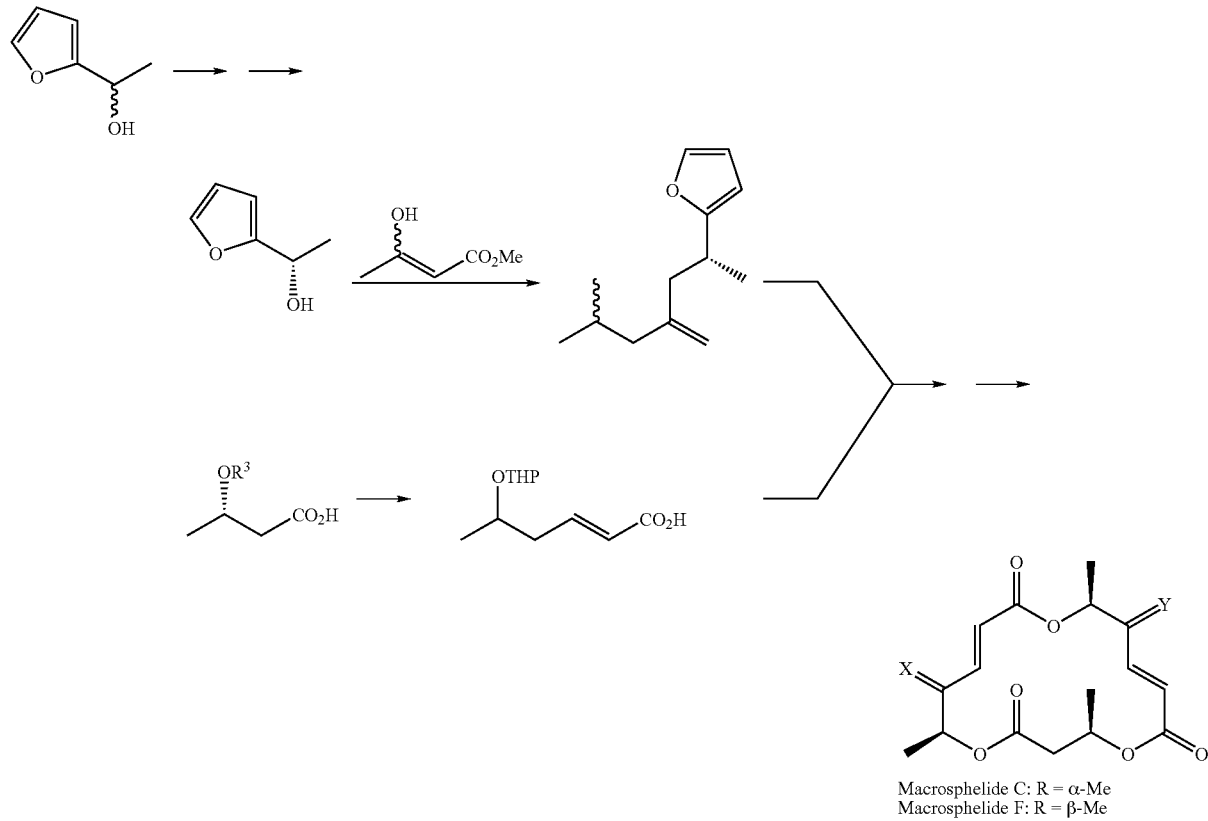

Recently, continuing research on macrosphelides has focused on the correlative relationship of their structure and effects with respect to not only biological adhesion inhibition activity, but also anti-virus activity and immunity suppression action. For this research, synthesis of natural and non-natural macrosphelides including derivatives and stereoisomers is essential. However, the synthesis methods for the above all use asymmetric induction reactions such as asymmetric oxidation or kinetic optical resolution, and the objective of the synthesis is to produce specific macrosphelides. Accordingly, application to other types of macrosphelides synthesis is not possible. Moreover, the above synthesis methods also suffer from the problem of having low yields of around 10%.

The present invention has been conceived of in light of the above described circumstances, and it is an object thereof to provide a new synthesis method that allows high yield synthesis of a macrosphelide core that provides a core for obtaining multiple different types of macrosphelide deviates.

DISCLOSURE OF THE INVENTION

As a new method for synthesizing macrosphelides, the inventors have investigated producing a macrosphelide core using methyl 3-hydroxybutyrate, for which both enantiomers can be easily commercially obtained, as a chiral building block. As a result, the present invention has been achieved based on the discovery that, by synthesizing a macrosphelide core with macrolactonization as a key reaction, it is possible to high yield synthesize a macrosphelides core that can be used as a material for synthesis of various derivatives, and, further, synthesize stereoisomers, and the like.

Accordingly, the invention disclosed in a first aspect of the present application is a synthesis method for macrosphelides, and relates to a method that is characterised by the following. Methyl 3-hydroxybutyrate, expressed by formula I, is prepared as a starting material,

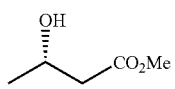

I and after the hydroxyl group of the methyl 3-hydroxybutyrate has been protected, it is reduced to alcohol. The alcohol is then oxidized to give 3-(tert-butyldimethylsilyloxy) butylaldehyde as expressed by the formula II,

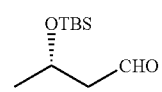

II

This aldehyde is then reacted with tert-butyl diethylphosphonoacetate to give an olefin, and then deprotected. Next, dehydrative condensation with diethylphosponoacetic acid is performed to give tert-butyl 5-[2-(diethylphosphonoyl) acetoxy] hex-2-enoate as expressed by formula III,

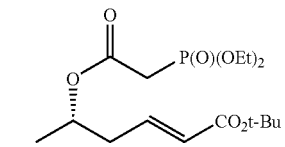

III

This compound is reacted with the 3-(tert-butyldimethylsilyloxy) butylaldehyde, as expressed by formula II, to form a diester, and then this diester is deprotected to give an alcohol as expressed by formula IV,

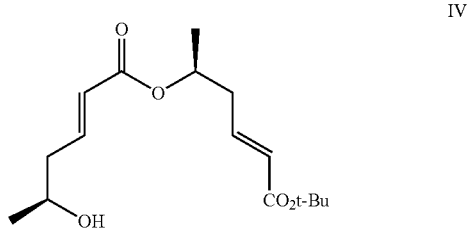

IV

The alcohol is dehydrated and condensed with 3-(tert-butyldimethylsilyloxy) butyric acid to give a triester, which is deprotected to give hydroxycarboxylic acid as expressed by formula V,

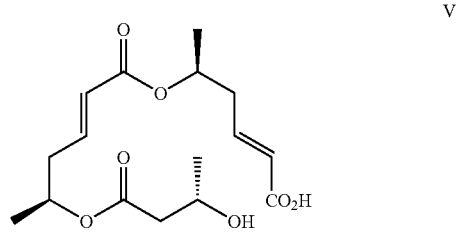

V

Then, macrolactonization of the hydroxycarboxylic acid is performed to obtain a macrosphelide core as expressed by formula VI,

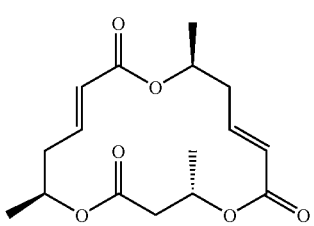

VI

With the above method, if methyl 3-hydroxybutyrate in S-form is used as the starting material, macrosphelides in S-form can be synthesized, whereas, on the other hand, if a starting material in R-form is used, macrosphelides in R-form can be synthesized.

Thus, the invention according to a second aspect of the application relates to a method for synthesizing an enantiomer of macrosphelides, and is characterised in that, in the synthesis method of the first aspect, a desired enantiomer is used for the methyl 3-hydroxybutyrate that is the starting material.

Moreover, it is possible to easily manufacture allylic position oxidants by oxidation of the allylic position of the macrosphelides obtained by the above method.

Thus, the invention according to a third aspect relates to a method for synthesizing allylic position oxidants of macrosphelides, and is characterised by oxidation of the allylic position of the macrosphelides obtained in accordance with the synthesis method for the first aspect.

BEST MODE FOR CARRYING OUT THE INVENTION

A synthesis method of the present invention uses methyl 3-hydroxybutyrate as a starting material. Both S-form and R-form enantiomers of this compound are commercially available, and both can be easily obtained.

With the synthesis method of the present invention it is usually necessary to protect the hydroxyl group. The protection can be carried out by, for example, introduction of tert-butyldimethylsilyl group. Further, deprotection by removal of the tert-butyldimethylsilyl group can be performed, for example, using trifluoroacetic acid in the presence of thioanisole.

The aldehyde expressed by formula II is unstable with respect to silica gel, and thus if column purification is carried out, the yield drops. Accordingly, it is preferable that, in the oxidation for forming the aldehyde, the removal of the by-products of the oxidant derivative is performed using a simple method, for example, Swern oxidation. The aldehyde expressed by formula II that is generated by the Swern oxidation can be used in the next reaction without performing column purification.

The process in which olefin is formed by reacting the aldehyde expressed by formula II with tert-butyl diethylphosphonoacetate, and the process in which diester is formed by reacting the aldehyde expressed by formula II and the compound expressed by formula III is preferably performed using a Horner-Emmons reaction. If this reaction is used, particularly in the former process, it is possible to obtain product in high yield. Further, it is possible to selectively generate just desired stereoisomers.

The synthesis method for macrosphelides of the present invention includes a total of 11 processes, and the overall yield thereof is around 35%. This is significantly higher than the roughly 10% yield of the conventional synthesis method mentioned above.

Moreover, the macrosphelides obtained by the synthesis method for the present invention can be used as starting materials for synthesis of a variety of macrosphelide derivatives. There are many macrosphelides that have oxygen functional group at the allylic position of the macrosphelide core. The oxidation of the allylic group of the macrosphelides expressed by formula VI can be carried out easily. The allylic oxidation is performed by, for example, using selenium dioxide as an oxidant in the 1,2-dichloroethane solvent, and refluxing under heating at 85° C. for 2 days.

Moreover, it is also possible to synthesize non-natural macrosphelides that are stereoisomers like enantiomer.

EXAMPLES

Hereinafter, the present invention will be concretely explained using the following example. However, the features of the invention are in no way limited thereto. The obtained products were analyzed using $^1$N-NMR, $^{13}$C-NMR, IR, mass spectrum, mass spectrometry, angle of rotation and elemental analysis.

Example 1

Synthesis of Macrosphelide Core

Process 1) Synthesis of (+)-methyl 3-(tert-butyldimethylsilyloxy) butyrate

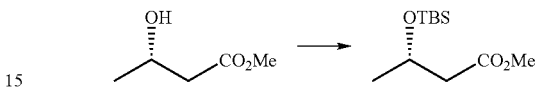

Tert-butyldimethylsilylchloride (1.8 g, 12 mmol) was added under an argon atmosphere at 0° C. to a dichloromethane (30 ml) solution of (+)-(S)-methyl 3-hydroxybutyrate (1.18 g, 10 mmol), triethylamine (3 ml) and 4-dimethylaminopyridine (catalyst amount), and then stirred for 13 hours at room temperature. Following this, the reaction solution was diluted using dichloromethane. Then, the organic layer, which had been washed in succession with 10% hydrochloric acid, saturated sodium bicarbonate water, and saturated saline solution, was dried over magnesium sulfate, filtered, and the solvent thereof was distilled off. The resulting residue was then separated using silica-gel column chromatography (hexane:ethyl acetate=99:1). The subject compound was obtained as a colorless oily matter (2.2 g, 95%).

$^1$H-NMR (300 MHz) (CDCl$_3$) δ: 4.26 (1H, m, 3-H), 3.66 (3H, s, COOMe), 2.48 (1H, dd, J=7.7 Hz, 14 Hz, 2-H), 2.37 (1H, dd, J=5.2 Hz, 14 Hz, 2-H), 1.19 (3H, d, J=6.0Hz, CH$_3$), 0.86 (9H, s, t-Bu-Si), 0.06 (3H, s, Me$_2$-Si), 0.04 (3H, s, Me$_2$-Si)

$^{13}$C-NMR (75 MHz) (CDCl$_3$) δ: 172.03 (s), 66.02 (d), 51.59 (q), 44.94 (t), 25.96 (q), 18.19 (s), −4.22 (q), −4.78 (q)

IR (neat): 1742 cm$^{-1}$ (C=O)

Mass spectrum: m/z 217 (M$^+$−15), 175 (M$^+$−57)

Mass spectrometry: With regard to C$_{10}$H$_{21}$O$_3$Si, Calculated value of 217.1210 (M$^+$−15), Measurement value of 217.1235; With regard to C$_7$H$_{15}$O$_3$Si, Calculated value of 175.0844 (M$^+$−57), Measurement value of 175.0817.

Angle of rotation: [α]$_D^{26}$+24.9 (c=0.925, CHCl$_3$)

Process 2) Synthesis of (+)-3-(tert-butyldimethylsilyloxy) butan-1-ol

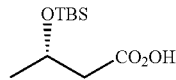

A hexane solution (1.0 M, 16 ml, 16 mmol) of diisobutylaluminium hydride (DIBAL) was added dropwise under an argon atmosphere at 0° C. into a dichloromethane (30 ml) solution of the (+)-methyl 3-(tert-butyldimethylsilyloxy butyrate (1.5 g, 6.5 mmol)) obtained by 1). Then, the solution was stirred for 2 hours at room temperature. Following this, saturated ammonium chloride water was added to the reaction solution, and following dilution with diethyl ether, the reaction solution was filtered through a Celite filter. The filtrate was dried over magnesium sulfate, and the solvent distilled off. The residue was then separated using silica-gel column chromatography (hexane:ethyl acetate=9:1), and the subject compound was obtained as a colorless oily matter (1.2 g, 92%).

$^1$H-NMR (300 MHz) (CDCl$_3$) δ: 4.06 (1H, m, 3-H), 3.79 (1H, m, 1-H), 3.68 (1H, m, 1-H), 2.71 (1H, s, OH), 1.73 (1H, m, 2-H), 1.60 (1H, m, 2-H), 1.16 (3H, d, J=6.0Hz, 4-H), 0.86 (9H, s, t-Bu-Si), 0.06 (3H, s, Me$_2$-Si), 0.04 (3H, s, Me$_2$-Si)

$^{13}$C-NMR (75 MHz) (CDCl$_3$) δ: 68.37 (d), 60.52 (t), 40.76 (t), 26.02 (q), 23.69 (q), 18.19 (s), −4.07 (q), −4.67 (q)

IR (neat): 3384 cm$^{-1}$ (OH)

Mass spectrum: m/z 147 (M$^+$−57)

Mass spectrometry: With regard to C$_6$H$_{15}$O$_2$Si, Calculated value of 147.0835 (M$^+$−57), Measurement value of 147.0838

Angle of rotation: [α]$_D^{26}$+24.1 (c=0.99, CHCl$_3$)

Process 3) Synthesis of
(+)-3-(tert-butyldimethylsilyloxy) butylaldehyde

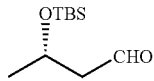

(a) Molecular sieve 4A (45.2 mg) and pyridinium dichromate (PDC) (45.2 mg, 1.2 mmol) were added under an argon atmosphere at 0° C. to a dichloromethane (10 ml) solution of the (+)-3-(tert-butyldimethylsilyloxy) butan-1-ol (200 mg, 0.98 mmol)) obtained by process 2). Then, the solution was stirred for 2 hours at room temperature. After the reaction was completed, the solvent was distilled off, and following dilution with diethyl ether, a Celite filter was used for filtering. The solvent of the filtrate was distilled off, and the residue was then separated using silica-gel column chromatography (hexane:ethyl acetate=100:1), and the subject compound was obtained as a colorless oily matter (79.1 mg, 40%).

(b) Dimethyl sulfoxide (DMSO) (1.08 ml, 15.12 mmol) was dissolved in a dichloromethane (28 ml) at room temperature under an argon atmosphere, and this solution was added to oxalyl chloride (0.88 ml, 10.08 mmol) at −78° C. Stirring was then performed for 10 minutes. Then (+)-3-(tert-butyldimethylsilyloxy) butan-1-ol (1.03 g, 5.04 mmol) was gradually added, and the solution was stirred for 1 hour. Following this, triethylamine (4.29 ml, 35.3 mmol) was added, the temperature was raised to 0° C., and stirring was performed for a further 15 minutes. The reaction solution was then diluted with diethyl ether, water was added, and extraction using diethyl ether was performed. Following this, the organic layer, which had been washed in succession with 10% hydrochloric acid, saturated sodium bicarbonate water, and saturated saline solution, was dried with magnesium sulfate, and filtered. The solvent thereof was distilled off. $^1$H-NMR measurement of the residue was then performed to check that the product was the subject compound, and then the product was used in the next reaction without performing any further purification.

$^1$H-NMR (300 MHz) (CDCl$_3$) δ: 9.76 (1H, dd, J=2.2 Hz, 2.7 Hz, CHO), 4.33 (1H, m, 3-H), 2.53 (1H, ddd, J=2.7 Hz, 6.9 Hz, 16 Hz, 2-H), 2.44 (1H, ddd, J=2.2 Hz, 4.9Hz, 16 Hz), 1.21 (3H, d, J=6.3 Hz, 4-H), 0.85 (9H, s, t-Bu-Si), 0.05 (3H, s, Me$_2$-Si), 0.04 (3H, s, Me$_2$-Si)

$^{13}$C-NMR (75 MHz) (CDCl$_3$) δ: 202.07 (t), 64.73 (d), 53.17 (t), 25.98 (q), 24.42 (q), 18.23 (s), −4.07 (q), −4.64 (q)

IR (neat): 1726 cm$^{-1}$ (C=O)

Mass spectrum: m/z 145 (M$^+$−57)

Mass spectrometry: With regard to C$_6$H$_{13}$O$_2$Si, Calculated value of 145.0685 (M$^+$−57), Measurement value of 145.0665

Angle of rotation: [α]$_D^{25}$+13.0 (c=0.95, CHCl$_3$)

Process 4) Synthesis of (+)-tert-butyl 5-(tert-butyldimethylsilyloxy) hex-2-enoate

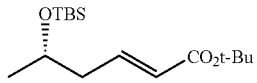

Tert-butyl diethylphosphonoacetate (1.31 ml, 5.55 mmol) and 1,8-diazabicyclo [5.4.0] undec-7-ene (0.693 ml, 5.04 mmol) were added to acetonitrile solution of lithium chloride (256 mg, 6.05 mmol) at 0° C. under an argon atmosphere. Then, the solution was stirred for 30 minutes. The (+)-3-(tert-butyldimethylsilyloxy) butylaldehyde obtained from (b) of process 3) above was added, and then stirring was performed for 1 hour at room temperature. Following this, the reaction solution was condensed, diluted with diethyl ether, and then washed in succession with 10% hydrochloric acid, saturated sodium bicarbonate water, and saturated saline solution. Then, the reaction solution was dried over magnesium sulfate, and filtered. The solvent thereof was distilled off, and the residue was then separated using silica-gel column chromatography (hexane:ethyl acetate=50:1), and the subject compound was obtained as a colorless oily matter (1.18 g, 2-process yield of 77% from process 2)).

$^1$H-NMR (300 MHz) (CDCl$_3$) δ: 6.82 (1H, dt, J=7.7, 15 Hz, 3-H), 5.73 (1H, dt, J=1.4, 15Hz, 2-H), 3.89 (1H, m, 5-H), 2.26 (2H, m, 4-H), 1.47 (9H, s, CO$_2$-t-Bu), 1.15 (3H, d, J=6.0 Hz, 6-H), 0.87 (9H, s, t-Bu-Si), 0.04 (6H, s, Me$_2$-Si)

$^{13}$C-NMR (75 MHz) (CDCl$_3$) δ: 165.82 (s), 144.81 (d), 125.04 (d), 80.15 (s), 67.96 (d), 42.58 (t), 28.42 (q), 26.11 (q) 24.13 (q), 18.39 (s), −4.20 (q), −4.50 (q)

IR (neat): 1716 cm$^{-1}$ (C=O), 1655 cm$^{-1}$ (C=C)

Mass spectrum: m/z 187 (M$^+$−57)

Mass spectrometry: With regard to C$_8$H$_{15}$O$_3$Si, Calculated value of 187.0860 (M$^+$−57), Measurement value of 187.0835

Angle of rotation: [α]$_D^{25}$+11.9 (c=1.27, CHCl$_3$)

Process 5) Synthesis of (+)-tert-butyl
5-hydroxyhex-2-enoate

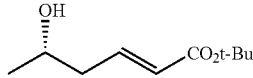

A THF solution (IM, 7.03 ml, 7.03 mmol) of tert-butylammonium fluoride (TBAF) was added to a THF (12 ml) solution of the (+)-tert-butyl 5-(tert-butyldimethylsilyloxy) hex-2-enoate (1.76 g, 5.86 mmol) under an argon atmosphere at room temperature. Then, stirring at room temperature was performed for 6 hours. Following this, the reaction solution was condensed, diluted with diethyl ether, washed in succession with water and saturated saline solution, dried over magnesium sulfate, and filtered. The solvent thereof was distilled off, and the residue was then separated using silica-gel column chromatography (hexane:ethyl acetate=4:1). The subject compound was obtained as a colorless oily matter (1.02 g, 95%).

$^1$H-NMR (300 MHz) (CDCl$_3$) δ: 6.83 (1H, dt, J=7.4, 15 Hz, 3-H), 5.71 (1H, dt, J=1.4, 15Hz, 2-H), 3.94 (1H, m, 5-H), 2.32 (2H, ddd, J=1.4, 6.3, 7.4 Hz, 4-H), 1.47 (9H, s, CO$_2$-t-Bu), 1.22 (3H, d, J=6.3 Hz, 6-H)

$^{13}$C-NMR (75 MHz) (CDCl$_3$) δ: 165.75 (s), 143.73 (d), 125.74 (d), 80.50 (s), 66.93 (d), 41.96 (t), 28.37 (q), 23.44 (q)

IR (neat): 3751 cm$^{-1}$ (OH), 1709 cm$^{-1}$ (C=O), 1653 cm$^{-1}$ (C=C)

Mass spectrum: m/z 142 (M$^+$–44), 130 (M$^+$–56)

Mass spectrometry: With regard to C$_8$H$_{14}$O$_2$Si, Calculated value of 142.0994 (M$^+$–44), Measurement value of 142,0992; With regard to C$_6$H$_{10}$O$_3$, Calculated value of 130.0630 (M$^+$–56), Measurement value of 130.0623

Angle of rotation: [α]$_D^{26}$+10.2 (c=1.17, CHCl$_3$)

Process 6) Synthesis of (–)-tert-butyl 5-[2-(diethylphosphonoyl) acetoxy] hex-2-enoate

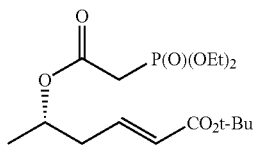

3-dicyclohexylcarbodiimide (DCC) (1.48 g, 7.14 mmol) was added to a dichloromethane (50 ml) solution of 4-dimethyl aminopyridine (DMAP) (62.3 mg, 0.51 mmol), diethylphosphono acetic acid (0.98 ml, 6.12 mmol) and the (+)-tert-butyl 5-hydroxyhex-2-enoate (950 mg, 5.10 mmol) obtained by process 5) at 0° C. under an argon atmosphere. Stirring was then performed for 30 minutes at room temperature. The solvent of the reaction solution was then distilled off, and following this diluted with diethyl ether and filtered through a Celite filter. The filtrate was then condensed, and the residue separated using silica-gel column chromatography (hexane:ethyl acetate=1:1). The subject compound was obtained as a colorless oily matter (1.78 g, 97%).

$^1$H-NMR (300 MHz) (CDCl$_3$) δ: 6.77 (1H, dt, J=7.5, 15 Hz), 5.80 (1H, d, J=15Hz), 5.04 (1H, m), 4.17 (4H, dq, J=7.1, 8.1 Hz), 2.95 (2H, d, J=21 Hz), 2.45 (2H, m), 1.48 (9H, s, t-Bu), 1.35 (6H, t, J=7.1 Hz), 1.27 (3H, d, J=6.3 Hz)

$^{13}$C-NMR (75 MHz) (CDCl$_3$) δ: 165.23 (s), 165.09 (s), 165.01 (s), 141.63 (d), 126.01 (d), 80.32 (s), 70.73 (d), 62.74 (t), 62.66 (t), 38.08 (t), 35.49 (t), 33.73 (t), 28.21 (q), 19.52 (q), 16.49 (q), 16.41 (q)

IR (neat): 1733 cm$^{-1}$ (C=O), 1654 cm$^{-1}$ (C=C)

Mass spectrum: m/z 364 (M$^+$)

Mass spectrometry: With regard to C$_{16}$H$_{29}$O$_7$P, Calculated value of 364.1651 (M$^+$), Measurement value of 364.1634

Angle of rotation: [α]$_D^{25}$–8.56 (c=1.32, CHCl$_3$)

Process 7) Synthesis of (+)-1-tert-butoxycarbonyl-pent-1-en-4-yl 5-(tert-butyldimethylsilyloxy) hex-2-enoate

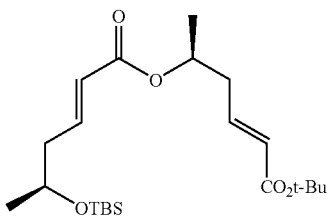

The (–)-tert-butyl 5-[2-(diethylphosphonoyl) acetoxy] hex-2-enoate (960 mg, 2.6 mmol) obtained from process 6) and 1,8-diazabicyclo [5.4.0] undec-7-ene (400 mg, 2.6 mmol) was added to an acetonitrile (30 ml) solution of lithium chloride (112 mg, 2.6 mmol) at 0° C. under an argon atmosphere. Stirring was performed for 30 minutes, and then the (+)-3-(tert-butyldimethylsilyloxy) butylaldehyde (450 mg, 2.2 mmol) obtained from process 3) was added and stirred for half an hour at room temperature. Following this, the reaction solution was condensed, diluted with diethyl ether, and then washed in succession with 10% hydrochloric acid, saturated sodium bicarbonate water, and saturated saline solution. Then, the reaction solution was dried over magnesium sulfate, filtered, and then the solvent thereof was distilled off. Then, the residue was separated using silica-gel column chromatography (hexane:ethyl acetate=95:5). The subject compound was obtained as a colorless oily matter (978 mg, 90%).

$^1$H-NMR (300 MHz) (CDCl$_3$) δ: 6.91 (1H, dt, J=7.5, 15 Hz), 6.85 (1H, dt, J=7.5, 15 Hz), 5.78 (2H, dt, J=1.4, 15 Hz), 5.03 (1H, m), 3.90 (1H, m), 2.44 (2H, m), 2.29 (2H, m), 1.45 (9H, s), 1.24 (3H, d, J=6.3 Hz), 1.14 (3H, d, J=6.0 Hz), 0.86 (9H, s), 0.03 (3H, s), 0.02 (3H, s)

$^{13}$C-NMR (75 MHz) (CDCl$_3$) δ: 165.72 (s), 165.52 (s), 146.35 (d), 142.31 (d), 125.92 (d), 123.33 (d), 80.40 (s), 69.18 (d), 67.80 (d), 42.67 (t), 38.53 (t), 28.37 (q), 26.06 (q), 24.10 (q), 19.89 (q), 18.34 (s), –4.22 (q), –4.51 (q)

IR (neat): 1719 cm$^{-1}$ (C=O), 1655 cm$^{-1}$ (C=C)

Mass spectrum: m/z 412 (M$^+$)

Mass spectrometry: With regard to C$_{22}$H$_{40}$O$_5$Si, Calculated value of 412.2646 (M$^+$), Measurement value of 412.2667

Angle of rotation: [α]$_D^{24}$+5.92 (c=1.07, CHCl$_3$)

Process 8) Synthesis of (+)-1-tert-butoxycarbonyl-pent-1-en-4-yl 5-hydroxy-hex-2-enoate

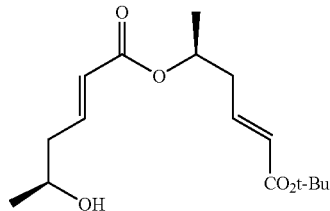

The silyl ether (5.11 g, 12.4 mmol) obtained by process 7) was stirred at room temperature for 3 days in an AcOH/THF/H$_2$O (3:1:1, 248 ml) solution. Following this, the reaction solution was extracted three times using CHCl$_3$. The organic layer thereof was washed with saturated sodium bicarbonate water, and then dried over magnesium sulfate. Then, after filtering, the solvent was distilled off, and the residue was then separated using silica-gel column chromatography (hexane:ethyl acetate=2:1) to obtain the subject compound as a colorless oily matter (3.50 g, 95%).

$^1$H-NMR (300 MHz) (CDCl$_3$) δ: 6.93 (1H, dt, J=7.4, 15 Hz), 6.75 (1H, dt, J=7.5, 15 Hz), 5.85 (1H, d, J=15 Hz), 5.76 (1H, d, J=15 Hz), 5.14 (1H, m), 3.94 (1H, m), 2.45 (2H, m), 2.33 (2H, m), 2.20 (1H, br, OH), 1.45 (9H, s), 1.24 (3H, d, J=6.3 Hz), 1.22 (3H, s), 1.20 (3H, s)

$^{13}$C-NMR (75 MHz) (CDCl$_3$) δ: 165.68 (s), 165.61 (s), 145.41 (d), 142.27 (d), 125.95 (d), 123.91 (d), 80.53 (s), 69.38 (d), 66.82 (d), 42.06 (t), 38.48 (t), 28.35 (q), 23.47 (q), 19.89 (q)

IR (neat): 3456 cm$^{-1}$ (OH), 1712 cm$^{-1}$ (C=O), 1654 cm$^{-1}$ (C=C)

Mass spectrum: m/z 298 (M$^+$)

Mass spectrometry: With regard to $C_{16}H_{26}O_5$, Calculated value of 298.1781 (M$^+$), Measurement value of 298.1779

Angle of rotation: $[\alpha]_D^{26}$+5.57 (c=0.86, CHCl$_3$)

Process 9) Synthesis of (−)-1-tert-butoxycarbonyl-pent-1-en-4-yl 5-[3-(tert-butyldimethylsilyloxy) butyryloxy]-hex-2-enoate

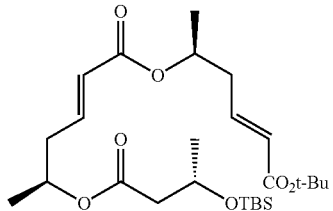

1,3-dicyclohexylcarbodiimide (DCC) (54.7 mg, 0.265 mmol) was added to a dichloromethane (20 ml) solution of 4-dimethyl aminopyridine (DMAP) (2.0 mg, 0.017 mmol), 3-(tert-butyldimethylsilyloxy) butyric acid (43 mg, 0.20 mmol) and the alcohol (50 mg, 0.17 mmol) obtained by process 8) at 0° C. under an argon atmosphere. Stirring was then performed for 3 hours at room temperature. The solvent of the reaction solution was then distilled off, and following this diluted with diethyl ether, and filtered through a Celite filter. The filtrate was then condensed, and the residue was then separated using silica-gel column chromatography (hexane:ethyl acetate=20:1). The subject compound was obtained as a colorless oily matter (80.6 mg, 94%).

$^1$H-NMR (300 MHz) (CDCl$_3$) δ: 6.95 (1H, dt, J=7.5, 15 Hz), 6.75 (1H, dt, J=7.7, 15 Hz), 5.83 (1H, d, J=15 Hz), 5.77 (1H, d, J=15 Hz), 4.97 (2H, m), 4.23 (1H, m), 2.45 (2H, m), 2.33 (2H, m), 2.30 (2H, m), 1.46 (9H, s), 1.25 (3H, d, J=6.8 Hz), 1.22 (3H, d, J=6.6 Hz), 1.16 (3H, d, J=6.0 Hz), 0.84 (9H, s), 0.05 (3H, s), 0.03 (3H, s)

$^{13}$C-NMR (75 MHz) (CDCl$_3$) δ: 170.88 (s), 165.51 (s), 165.41 (s), 143.73 (d), 142.19 (d), 125.95 (d), 124.33 (d), 80.45 (s), 69.43 (d), 69.22 (d), 65.85 (d), 45.19 (t), 38.56 (t), 38.46 (t), 28.35 (q), 26.01 (q), 24.03 (q), 19.88 (q), 19.78 (q), 18.23 (s), −4.22 (q), −4.62 (q)

IR (neat): 1722 cm$^{-1}$ (C=O), 1656 cm$^{-1}$ (C=C)

Mass spectrum: m/z 498 (M$^+$)

Mass spectrometry: With regard to $C_{26}H_{46}O_7Si$, Calculated value of 498.3013 (M$^+$), Measurement value of 498.3012

Angle of rotation: $[\alpha]_D^{25}$−1.34 (c=0.88, CHCl$_3$)

Process 10) Synthesis of (−)-5-[5-(3-hydroxybutyloxy) hex-2-enoyloxy] hex-2-enoic acid

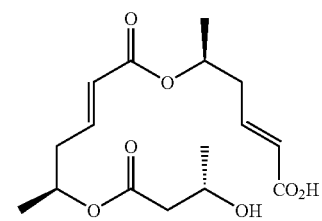

Thioanisole (12.5 ml) and trifluoroacetic acid (2.5 ml) were added to a dichloromethane (12.5 ml) solution of the silyloxy ester (500 mg, 1.00 mmol) obtained by process 9) at 0° C. under an argon atmosphere, and then stirred for 1 hour at room temperature. This reaction solution was condensed, and then the residue was separated using silica-gel column chromatography (chloroform:methanol=20:1). The subject compound was obtained as a colorless oily matter (273.4 mg, 83%).

$^1$H-NMR (300 MHz) (CDCl$_3$) δ: 6.97 (1H, dt, J=7.1, 15 Hz), 6.85 (1H, dt, J=7.5, 15 Hz), 5.88 (1H, d, J=15 Hz), 5.83 (1H, d, J=15 Hz), 5.12 (2H, m), 4.28 (1H, m), 2.44 (6H, m), 1.28 (3H, d, J=6.3 Hz), 1.26 (3H, d, J=5.7 Hz), 1.22 (3H, d, J=6.3Hz)

$^{13}$C-NMR (75 MHz) (CDCl$_3$) δ: 172.22 (s), 170.31 (s), 165.48 (s), 146.13 (d), 143.89 (d), 124.27 (d), 123.67 (d), 69.76 (d), 69.24 (d), 64.59 (d), 43.16 (t), 38.64 (t), 38.77 (t), 22.66 (q), 20.05 (q), 20.01 (q)

IR (neat): 3455 cm$^{-1}$ (OH), 2978 cm$^{-1}$ (CO$_2$H), 1713 cm$^{-1}$ (C=O), 1656 cm$^{-1}$ (C=C)

Mass spectrum: m/z 328 (M$^+$)

Mass spectrometry: With regard to $C_{16}H_{24}O_7$, Calculated value of 328.1522 (M$^+$), Measurement value of 328.1511

Angle of rotation: $[\alpha]_D^{25}$−8.31 (c=1.43, CHCl$_3$)

Process 11) Synthesis of Macrosphelide Core

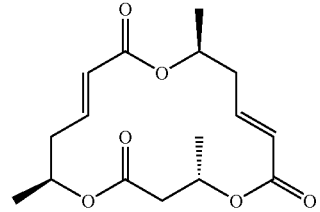

Triethylamine (73 mg, 0.72 mmol) and 2,4,6-trichlorobenzoyl chloride (146 mg, 0.6 mmol) were added to a toluene (10 ml) solution of the (−)-5-[5-(3-hydroxybutyloxy) hex-2-enoyloxy] hex-2-enoic acid (40 mg, 0.12 mmol) under an argon atmosphere at room temperature, and then the solution was stirred for 1 hour. Following this, the reaction solution was diluted using toluene (20 ml), and the diluted solution was heated to 80° C., and then gradually added dropwise over two hours into a toluene (10 ml) solution of 4-dimethyl aminopyridine (DMAP) (170 mg, 1.4 mmol). When drip addition was completed, the reaction solution was cooled, saturated sodium bicarbonate water was added, and extraction using ethyl acetate performed. The organic layer thereof was then dried with magnesium sulfate, and, after filtering, the solvent was distilled off. The obtained residue was then separated using silica-gel column chromatography (hexane:ethyl acetate=1:1) to obtain the subject compound as a colorless oily matter (34 mg, 90%). The melting point was 94 to 95° C. (colorless flake-like crystals, hexane).

$^1$H-NMR (300 MHz) (CDCl$_3$) δ: 6.88~6.74 (2H, m), 5.78 (2H, dt, J=1.5, 15 Hz), 5.35 (1H, m), 5.13~5.01 (2H, m), 2.62~2.25 (6H, m), 1.34 (3H, d, J=6.3 Hz), 1.29 (3H, d, J=6.3 Hz), 1.26 (3H, d, J=6.3 Hz)

$^{13}$C-NMR (75 MHz) (CDCl$_3$) δ: 170.15 (s), 165.33 (s), 164.94 (s), 144.62 (d), 143.52 (d), 124.95 (d), 123.77 (d), 70.26 (d). 68.75 (d), 67.85 (d), 41.72 (t), 39.62 (t), 39.10 (t), 21.30 (q), 20.83 (q), 20.35 (q)

IR (neat): 1727 cm$^{-1}$ (C=O), 1657 cm$^{-1}$ (C=C)

Mass spectrum: m/z 310 (M$^+$)

Mass spectrometry: With regard to $C_{16}H_{22}O_6$, Calculated value of 310.1417 ($M^+$), Measurement value of 310.1404

Angle of rotation: $[\alpha]_D^{25}$+15.9 (c=0.82, $CHCl_3$)

Elemental analysis: With regard to $C_{16}H_{22}O_6$, Calculated value of C, 61.92; H, 7.15; Measurement value of C, 61.91; H, 7.00;

INDUSTRIAL APPLICABILITY

According to the synthesis method for the present invention, it is possible to synthesize natural or non-natural macrosphelides with a markedly improved yield, as compared to conventional methods. Further, the macrosphelides can be used as a core for manufacturing a variety of derivatives. Moreover, by changing the starting material, it is easily possible to synthesize stereoisomers like enantiomer.

Macrosphelides, as well as derivatives and stereoisomers, manufactured in this way are useful for investigation of the specific details of the correlative relationship between macrosphelide structure and effects. This will allow cell adhesion inhibition activity as well as anti-virus activity and immunity suppression action to be clarified, which can be expected to provide assistance in discovering new usages for macrosphelides.

The invention claimed is:

1. A method for synthesizing macrosphelides, characterised by:

preparing methyl 3-hydroxybutyrate, expressed by formula I, as a starting material,

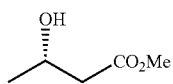

I forming 3-(tert-butyldimethylsilyloxy) butylaldehyde, as expressed by formula II, by protecting hydroxyl group of the methyl 3-hydroxybutyrate, then performing reduction to alcohol, and then oxidizing the alcohol,

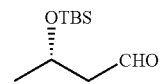

II forming tert-butyl 5-[2-(diethylphosphonoyl) acetoxy] hex-2-enoate, as expressed by formula III, by reacting the aldehyde with tert-butyl diethylphosphonoacetate to give an olefin, then performing deprotection, and then dehydrating and condensing with diethylphosphonoacetic acid,

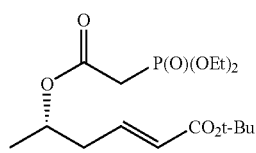

III forming an alcohol, as expressed by formula IV, by reacting the compound with the aldehyde expressed by formula II to form a diester, and then performing deprotection,

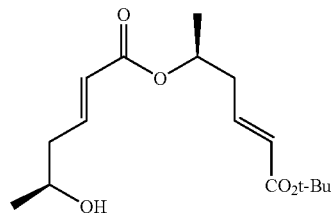

IV forming hydroxycarboxylic acid, as expressed by formula V, by dehydrating and condensing the alcohol with 3-(tert-butyldimethylsilyloxy) butyric acid to give a triester, and then performing deprotection,

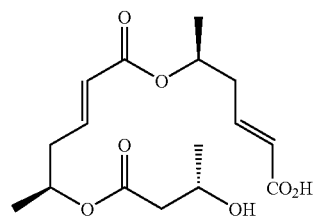

V obtaining a macrosphelide core, as expressed by formula VI, by macrolactonization of the hydroxycarboxylic acid,

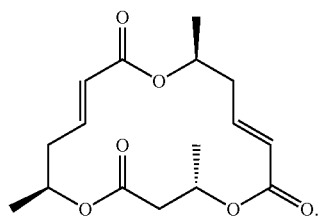

VI

2. A method for synthesizing enantiomer of macrosphelides, characterised by:

in the synthesis method according to claim 1, using a desired enantiomer for the methyl 3-hydroxybutyrate that is the starting material.

3. A method for synthesizing allylic position oxidants of macrosphelides, characterised by:

oxidizing the allylic position of the macrosphelides obtained in accordance with the synthesis method according to claim 1.

* * * * *